United States Patent [19]

Alman

[11] Patent Number: 4,479,718
[45] Date of Patent: Oct. 30, 1984

[54] THREE DIRECTION MEASUREMENTS FOR CHARACTERIZATION OF A SURFACE CONTAINING METALLIC PARTICLES

[75] Inventor: David H. Alman, Royal Oak, Mich.

[73] Assignee: E. I. Du Pont de Nemours and Company, Wilmington, Del.

[21] Appl. No.: 389,287

[22] Filed: Jun. 17, 1982

[51] Int. Cl.³ .............................................. G01J 3/46
[52] U.S. Cl. .................................................. 356/405
[58] Field of Search ................ 356/405, 402; 364/498, 364/526

[56] References Cited

U.S. PATENT DOCUMENTS

| | | | |
|---|---|---|---|
| 3,389,265 | 6/1965 | Schreckendgust | 250/226 |
| 3,690,771 | 9/1972 | Armstrong et al. | 356/405 |
| 3,712,745 | 1/1973 | Armstrong et al. | 356/244 |
| 3,916,168 | 10/1975 | McCarty et al. | 356/405 |

*Primary Examiner*—F. L. Evans
*Attorney, Agent, or Firm*—Hilmar L. Fricke

[57] ABSTRACT

An improved method for instrumentally characterizing the optical properties of a surface containing metallic particles such as a paint containing metallic flakes by using multiangular spectrophotometric or colormetric measurements to derive color constants for the paint, wherein the improvement comprises using three multiangular measurements, preferably 15°, 45° and 110° as measured from the specular angle.

3 Claims, 2 Drawing Figures

THREE DIRECTION MEASUREMENTS FOR CHARACTERIZATION OF A SURFACE CONTAINING METALLIC PARTICLES

BACKGROUND OF THE INVENTION

In the manufacture of pigmented finishes one rarely if ever achieves a satisfactory color match versus a color standard without an adjustment process known as shading. Shading usually involves a relatively minor but critical manipulation of the formula pigment composition, correcting for the cumulative effects of manufacturing variables on pigment dispersions.

Traditionally, the shading process has been carried out by highly skilled and trained personnel who require extensive on-the-job experience to achieve proficiency in their craft. Since visual shading at best is an art, effective administration of the process was difficult.

In more recent years, such visual shading has been supplemented by the use of apparatuses for instrumentally characterizing a paint or pigment composition. Colorimeters and spectrophotometers are well-known in the art and are used to measure certain optical properties of various paint films which have been coated over test panels. A typical spectrophotometer provides for the measurement of the amount of light reflected at varying light wavelength in the visible spectrum by a painted panel that is held at a given angle relative to the direction of an incident source of light. The reflectance factor of the paint enables paint chemists to calculate color values by which to characterize various paint colors. For a paint containing no light-reflecting flakes or platelets (i.e., non-metallic paints), the reflectance factor will not vary with the angle of the panel relative to the direction of incident light except at the gloss (specular) angle. Consequently, a single spectrophotometric reading at any specified angle will produce a reflectance value by which to accurately characterize the paint.

However, the paint industry often utilizes light-reflecting flakes in paints (i.e., metallic paints) to obtain pleasing aesthetic effects. Paints containing light-reflecting flakes of such materials as aluminum, bronze, coated mica and the like are characterized by a "two-tone" or "flip-flop" effect whereby the apparent color of the paint changes at different viewing angles. This effect is due to the orientation of the flakes in the paint film. Since the color of such metallic paints will apparently vary as a function of the angle of illumination and viewing, a single spectrophotometric reading is inadequate to accurately characterize the paint. Although measurement studies have shown that visual color differences existing between two metallic paints were detectable at an infinite number of angles, it is obvious that practical reasons preclude the collection of reflectance factors for an infinite number of viewing angles. However, previous studies have also indicated that measurement of the optical properties of a metallic paint at only two specified angles can provide useful characterization. See, for example, U.S. Pat. No. 3,690,771, issued Sept. 12, 1972 to Armstrong, Jr., Edwards, Laird, and Vining, the disclosure of which is herein incorporated by reference.

The present invention relates to the discovery that unexpectedly improved optical characterization of metallic paints results when measurements are taken at three specified angles.

SUMMARY OF THE INVENTION

There is provided by the present invention an improved method for instrumentally characterizing the optical properties of a surface containing metallic particles such as paint-containing metallic particles or flakes by using multiangular spectrophotometric or colorimetric measurements to derive color constants for the paint, wherein the improvement comprises using three multiangular measurements.

DETAILED DESCRIPTION OF THE INVENTION

Figure 1:
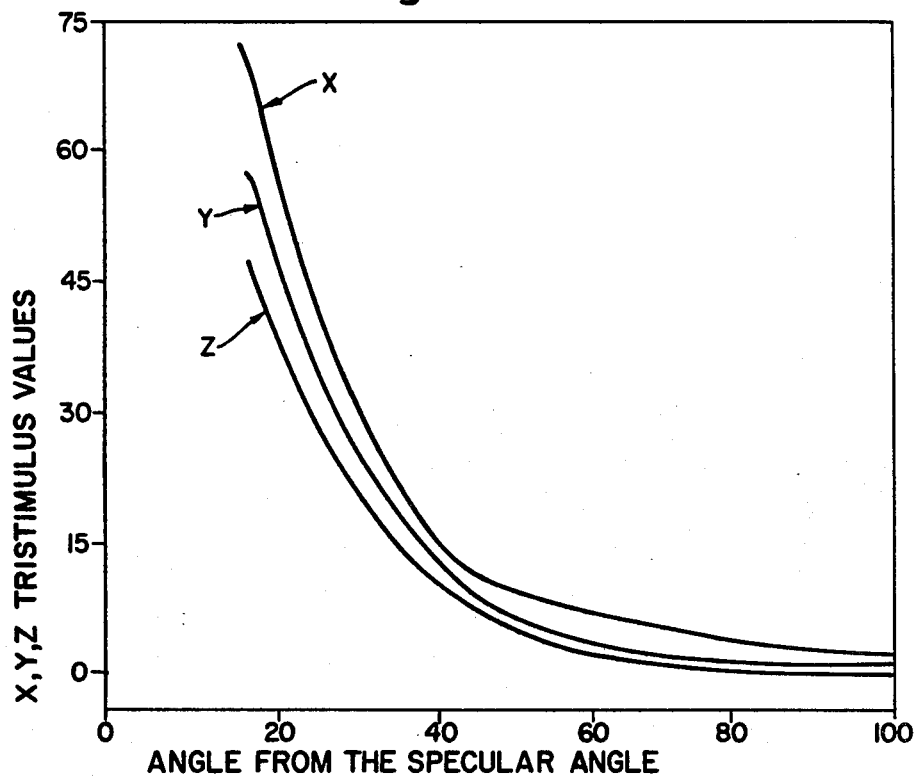
FIG. 1 is a graphic representation of the angular dependence of tristimulus values.

In optically characterizing surfaces containing metallic particles such as metallic paints and films, it was recognized that directional reflectance had to be considered. Metallic paints contain light-reflecting flakes or platelets of such material as aluminum, bronze, coated mica and the like. These flakes or platelets function much like little mirrors, reflecting light directionally rather than in a diffuse manner. The directional reflectance characteristic of a metallic paint film results in a phenomenon known as goniochromatism, which is defined as the variation in color of a paint film as a function of the directions of illumination and viewing. This phenomenon is also sometimes described as "two-tone", "flop", "flip-flop", "flash", "side-tone", etc. In sum, the color of a metallic paint will appear different at different viewing angles.

To account for this directional or angular reflectance, i.e, goniochromatism, spectrophotometrically determined reflectance factors must be taken multiangularly. The reflectance factor of a paint film is the ratio of the light flux reflected from the film sample to the light flux reflected from a perfect reflecting diffuser when the sample and perfect diffuser are identically irradiated. A perfect white reflector has a value of 1. A perfect black nonreflector has a value of 0.

The reflectance factors are used to calculate color descriptor values used to specify color and color difference. The tristimulus values (X, Y, Z) of a color are calculated by combining the reflectance factor data (R) with data on the sensitivity of the human eye ($\bar{x}, \bar{y}, \bar{z}$) and the irradiance of a light source (E) all as functions of wavelength ($\lambda$) in the visible spectrum. The defining equations for tristimulus values are:

$$X = \int_{360}^{830} R(\lambda) E(\lambda) \bar{x}(\lambda) \, d\lambda$$

$$Y = \int_{360}^{830} R(\lambda) E(\lambda) \bar{y}(\lambda) \, d\lambda$$

$$Z = \int_{360}^{830} R(\lambda) E(\lambda) \bar{z}(\lambda) \, d\lambda$$

The tristimulus values can be used to calculate color descriptors which relate to visual perception of color and color difference. One of many sets of descriptors which can be used are the CIELAB perceptual color scales recommended by the International Commission on Illumination ("Recommendations on Uniform Color Spaces, Color Difference Equations, Psychometric Color Terms", Supplement No. 2 To CIE Publication No. 15 (E1.3.1) 1971/CT(1.3) 1978. Bureau Central De La CIE, 52, Boulevard Malesherbes 75008, Paris, France).

Transformations of the tristimulus values can be used to calculate perceptual color values describing lightness (L*), redness/greenness (a*), yellowness/blueness (b*), saturation (C) or hue (H). A color can be completely described by a set of L, a, b or L, C, H values. The following equations which have been specified by the International Committee on Illumination relate the tristimulus values to L*, a* and b*

$$L^* = 116(Y/Y_o)^{1/3} - 16$$

$$a^* = 500[(X/X_o)^{1/3} - (Y/Y_o)^{1/3}]$$

$$b^* = 200[(Y/Y_o)^{1/3} - (Z/Z_o)^{1/3}]$$

where

Xo, Yo and Zo are the tristimulus values of the perfect white for a given illuminant;

X, Y and Z are the tristimulus values for the color.

The saturation (C) and hue (H) descriptors are related to the a* and b* values as follows:

$$C = (a^{*2} + b^{*2})^{1/2}$$

$$H = \tan^{-1}(b^*/a^*)$$

Often it is necessary to compare a color such as a sample batch of paint to a standard color and determine the difference and then adjust the sample with appropriate additives to bring the sample within tolerance values of the standard. The difference in color between a color standard and a batch sample is described as follows:

$$\Delta L^* = L^*(\text{batch}) - L^*(\text{standard})$$

$$\Delta a^* = a^*(\text{batch}) - a^*(\text{standard})$$

$$\Delta b^* = b^*(\text{batch}) - b^*(\text{standard})$$

The resultant values agree with the visual assessments of differences in lightness (ΔL*), redness/greenness (Δa*) and yellowness/blueness (Δb*).

Further discussion will employ the tristimulus values (X, Y, Z) and perceptual color values (L*, a*, b*, C, H) to quantify the influence of changing conditions of illumination and viewing on measurement of goniochromatic color. The specific color descriptors employed are only one of many possible choices of transformations of tristimulus values which could be employed in this task.

The tristimulus values, and hence the L*, a*, b* values as well, for a metallic paint vary in a regular manner with regular variation in the angle of viewing the paint film. In FIG. 1, the directional color behavior of a solution lacquer medium red metallic color is shown. The sample was prepared by conventional air atomized spray onto an aluminum substrate followed by a 155° C. bake for 30 minutes. Reflectance factor measurements relative to a standard white (BaSO4) were made in six sets of irradiation and viewing directions using a reflection spectrophotometer specifically designed to measure reflection properties with variable measurement geometry. This instrument is essentially a standard spectrophotometer consisting of a lightsource, monochromator, variable measurement geometry module, light detector and associated control and readout electronics. The reflectance factor for each measurement geometry was used to calculate tristimulus values as previously described. In FIG. 1, the angular dependence of tristimulus values, X, Y and Z is illustrated. The angle is measured from the specular (or "mirror") angle.

The values used for FIG. 1 are as follows:

| Measurement Angle From the Specular Angle (degrees) | Tristimulus Values | | |
|---|---|---|---|
| | X | Y | Z |
| 15 | 67.6 | 57.2 | 46.5 |
| 35 | 21.2 | 17.3 | 13.3 |
| 45 | 12.9 | 10.3 | 7.7 |
| 55 | 8.4 | 6.7 | 4.8 |
| 75 | 5.0 | 3.9 | 2.6 |
| 95 | 3.6 | 2.8 | 1.9 |

Analysis of the angular dependence plot of FIG. 1 reveals three things:

(1) Tristimulus values are not constant with angle variation, hence values from multiple angle measurements are necessary to accurately describe the color behavior of the sample;

(2) The plots are monotonically decreasing functions as the angle from specular increases, therefore a simple mathematical model should describe the curve; and (3) The plots are curved such that the mathematical model should probably be one higher than of the first order (linear).

Similar angular dependence plots have been obtained for a wide variety of metallic colors and all show similar results. The significance of these results is that they define the metallic color characterization and specification problem. Since all metallic colors show similar curved, monotonically decreasing tristimulus values as functions of the measurement direction from the specular angle, there is a systematic angular color behavior for which a simple measurement strategy can be developed. Multiple measurements will be required to adequately characterize this behavior.

Since L*, a*, and b* are the color values usually employed to characterize the color of paint films, it is of prime importance to determine the number of measurements needed to satisfactorily characterize the angular dependence of these values. Plots of all three variables are adequately similar, so that it is reasonable to assume that a mathematical characterization that fit a plot of the angular dependence of L* would also fit a plot of the angular dependence of a* and b*.

The optimum fit of various mathematical models to a lightness (L*) angular dependence curve is of the second order, which requires three measurements.

This can be shown by considering the mean residual error in L* value at six sets of measuring directions as predicted by various prediction models employing subsets of the six measuring directions.

The reflectance factors in 6 measurement geometries for 37 solution lacquer metallic colors were determined and the lightness values, L*, for these geometries calculated. The samples were prepared and measured as previously described. The objective is to define a metallic color characterization system which provides optimum information for minimum effort. This is done by considering whether subsets of the 6 measurement geometry data are adequate to predict the color lightness behavior at all 6 geometries. A linear metallic color characterization model is developed based on a first order equation. Such equations for the angular dependence of metallic lightness have the form:

$$*L = a_1 + a_2\phi$$

where L* is lightness, $\phi$ is angle from the specular angle and $a_1$ and $a_2$ are constants specific to each color which are fit from measurements using at least two different measurement directions. Similarly, a quadratic (second order) equation is used having the form:

$$*L = a_1 + a_2\phi + a_3\phi^2$$

where the variables are the same as in the linear example with the addition of another constant $a_3$. A minimum of three measurement directions are now required. Table I indicates the mean sum of squares residual for 6 measurement geometries with 37 metallic colors with several metallic characterization models. When the mean sum of squares residual is low, a model which describes the color dependence of metallic color on measurement direction has been found.

TABLE I

Influence of measurement direction selection on metallic color lightness prediction.

| Model (Order) | Number of Measurement Directions | Mean Sum of Squares Residual for 6 Measurement Directions. |
| --- | --- | --- |
| Linear (1) | 2 | 529.3 |
| Quadratic (2) | 3 | 12.5 |
| Quadratic (2) | 4 | 9.9 |
| Quadratic (2) | 5 | 8.5 |

Addition of just one more measurement, taken nearer to the specular angle, decreases the sum of the squares error of prediction from 529.3 to 12.5 in L* units. This indicates that the metallic color lightness behavior at any direction can be well predicted from measurements at 3 selected directions.

Higher accuracy can be achieved by adding more measurement angles or by going to a higher order equation with more measurement angles, but no such move will lead to the dramatic and surprising increase in accuracy attainable by utilizing a second order model incorporating just one more angle measurement than in the 2-angle system. That is, three properly selected measurement directions are an optimized selection to give maximum information on metallic color for minimum measurement effort. The example data describe the optimization results for lightness values. Similar results are obtained for tristimulus values (X, Y, Z), perceptual color values (a*, b*, C, H), color difference values ($\Delta L^*$, $\Delta a^*$, $\Delta b^*$) or other transformation from tristimulus values.

In collecting data on the optical characterization of a paint film, a variety of measurement techniques can be used. One technique is object modulated reflectance (OMR) wherein the light source and viewer or detector reference point are fixed and the object position is varied. This technique is exemplified in U.S. Pat. No. 3,712,745, issued Jan. 23, 1973 to Armstrong, Jr., Edwards, and Vining, herein incorporated by reference.

Two other techniques are Detector Modulated Reflectance (DMR) and Illuminant Modulated Reflectance (IMR). In DMR, the detector is varied while the light source and object are fixed. And in IMR, the illuminant or light source is varied, while detector and object remain fixed.

As discussed earlier, analysis of data (collected by use of DMR) indicated that the optimum set of measurements to characterize the goniochromatic effect in metallic paint films consists of measurements taken at three angles: (1) near the specular angle; (2) about 45° from the specular angle; and (3) far from the specular angle. In general, for a typical metallic color, the angular dependence of L*, C, H values is of the second order for any set of angles varying regularly from near specular to far from specular, whether measured by OMR, DMR, IMR or some combination of these. Hence, whether OMR, DMR, or IMR is utilized, three measurements can optimally characterize the L*, C, H angular dependence curves.

Figure 2:
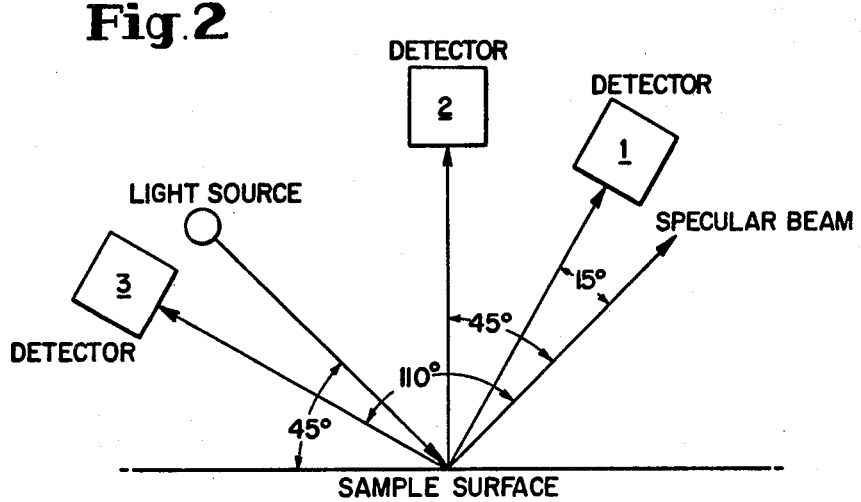
FIG. 2 is a schematic representation of a preferred spectrophotometric system embodying the method of the present invention.

FIG. 2 represents a preferred embodiment of the invention wherein DMR is utilized. The incident light source is positioned at an angle of 45° relative to the paint film. Three detectors are positioned in order to take optical property measurements at three different angles (as measured from the specular angle):

(1) Detector No. 1—15° (near specular);
(2) Detector No. 2—45° (perpendicular to the paint film surface); and
(3) Detector No. 3—110° (far from specular).

While the same angles may not be chosen for a system utilizing IMR or OMR, suitable angles could be easily determined by one skilled in the art.

The improved method of this invention can be used to characterize not only metallic paint films but any surface containing metallic particles, such as plastics containing reflective metallic flakes. The improved method is particularly useful in shading paint wherein the L*, a* and b* values are determined for a standard. Then a batch of paint is manufactured according to a given formula; a painted panel of the batch is made and the L*, a* and b* values are determined. Often the batch of paint, even if carefully made, does not match the standard because of variations in pigments and color drift of pigment dispersions. The $\Delta L^*$, $\Delta a^*$ and $\Delta b^*$ values of the batch are calculated and if outside of an acceptable tolerance value, calculations are made for the addition of pigments in the form of mill bases and the mill bases added to the batch and a second panel prepared and values are measured as above. The process is repeated until there is an acceptable color match between the standard and the batch of paint.

What is claimed is:

1. An improved method for instrumentally characterizing the optical properties of a paint film containing metallic flakes by using multiangular spectrophotometric measurements to derive color constants for the paint, wherein the improvement comprises using three multiangular measurements utilizing the techniques of Detector Modulated Reflectance, taken at angles of about 15°, 45°, and 110°, as measured from the specular angle with an illumination angle of 45° relative to the metallic paint film being optically characterized and determining X, Y and Z tristimulus values of a paint film by using the following equations:

$$X = \int_{360}^{830} R(\lambda) E(\lambda) \bar{x}(\lambda) d\lambda$$

$$Y = \int_{360}^{830} R(\lambda) E(\lambda) \bar{y}(\lambda) d\lambda$$

$$Z = \int_{360}^{830} R(\lambda) E(\lambda) \bar{z}(\lambda) d\lambda$$

wherein
R is the reflectance factor data,
$\bar{x}, \bar{y}, \bar{z}$ data on the sensitivity of the human eye,
E is the irradiance of a light source and
$\lambda$ function of wavelength in the visible light spectrum from 360–830 nanometers.

2. The improved method of claim 1 in which perceptual color values of a paint film of lightness (L*), redness/greenness (a*), yellowness/blueness (b*), saturation (C) and hue (H) are determined using the following equations:

$$L^* = 116(Y/Yo)^{1/3} - 16$$

$$a^* = 500[(X/Xo)^{1/3} - (Y/Yo)^{1/3}]$$

$$b^* = 200[(Y/Yo)^{1/3} - (Z/Zo)^{1/3}]$$

$$C = (a^{*2} + b^{*2})^{1/2}$$

$$H = \tan^{-1}(b^*/a^*)$$

where Xo, Yo and Zo are tristimulus values of a perfect white for a given illuminant; X, Y and Z are tristimulus values of color.

3. An improved method for instrumentally characterizing the optical properties of a metallic paint film, as recited in claim 2 wherein said method is one step in a method for shading metallic paints.

* * * * *